United States Patent [19]

Woo

[11] Patent Number: 4,567,005
[45] Date of Patent: Jan. 28, 1986

[54] ALLYLATION OF CARBON ACIDS

[75] Inventor: Edmund P. Woo, Midland, Mich.

[73] Assignee: The Dow Chemical Company, Midland, Mich.

[21] Appl. No.: 487,481

[22] Filed: Apr. 22, 1983

[51] Int. Cl.$^4$ .................... C07C 121/70; C07C 49/203
[52] U.S. Cl. ............................ 260/465 D; 260/465 K;
560/190; 560/211; 568/312; 568/388; 568/927;
568/943; 585/534
[58] Field of Search ................................ 560/190, 211;
260/465 K, 465 D, 465.9; 568/312, 388, 927,
943; 585/534

[56] References Cited

U.S. PATENT DOCUMENTS 4,362,670 12/1982 Woo ..................................... 560/190

FOREIGN PATENT DOCUMENTS 13663 7/1980 European Pat. Off. .

OTHER PUBLICATIONS

K. Takahashi et al., Bull. Chem. Soc. Japan, 45, 230 (1972).
K. E. Atkins, Tet. Lett., 43, 3821–3824 (1970).
House, *Modern Synthetic Reactions*, W. A. Benjamin, Inc., 494, (1972).
J. C. Fiaud et al., Tet. Lett., 21, 4437–4440 (1980).
J. P. Genet et al., Tet. Lett., 21, 3183–3186 (1980).
J. Tsuji et al., Tet. Lett., 49, 4387–4388 (1965).

*Primary Examiner*—Nicky Chan

[57] ABSTRACT

Carbon acids are allylated by contacting with an allyl carbonate in the presence of an iron, cobalt, nickel, ruthenium, rhodium, osmium, iridium or platinum catalyst.

12 Claims, No Drawings

ALLYLATION OF CARBON ACIDS

BACKGROUND OF THE INVENTION

The present invention relates to an improved process for the allylation of carbon acids without the use of base. More particularly, the present invention comprises the reaction of carbon acids with allyl carbonates in the presence of molybdenum, tungsten, cobalt, nickel, ruthenium, rhodium, osmium, iridium or platinum catalysts.

It is already known to form allylic derivatives of carbon acids by contacting the same with allylic alcohols, amines or esters in the presence of homogeneous palladium catalysts. See, K. E. Atkins, *Tetrahedron Letters*, 43, 3821-3824 (1970). While the process has been found suitable for strongly acid compounds such as acetylacetone it has not been found suitable for allylation of less acidic compounds such as dialkyl malonates or phenylacetonitrile. Besides resulting in no or very little conversion of the acid compounds, the reactants reduce the homogeneous catalyst resulting in a metallic precipitate.

An improved process for the allylation of carbon acids which allows for the allylation of relatively weak carbon acids is desired. Further, a process that does not detrimentally affect the catalyst system is desired.

SUMMARY OF THE INVENTION

According to the present invention an improved process for the allylation of carbon acids is provided. The invented process comprising reacting the carbon acid with an allyl carbonate in the presence of a metal catalyst selected from the group consisting of molybdenum, tungsten, cobalt, ruthenium, rhodium, osmium, iridium or platinum catalyst. The process results in improved reaction times and lowered reaction temperatures compared to previously known processes. Also, the process for the first time allows the artisan to form allyl derivatives of carbon acids that have heretofore not been capable of allylation without the use of strong base.

The invented process provides a useful method for the preparation of substituted carbon acids from base sensitive reactants. Furthermore, the compounds prepared by the present process find use in various applications in industry as monomers capable of polymerization or copolymerization through the ethylenically-unsaturated allyl functionality to form resins useful in the manufacture of solid articles and as intermediates for preparing herbicides, insecticides and other useful chemicals.

DETAILED DESCRIPTION OF THE INVENTION

The allyl carbonates for use according to the invention are of the formula:

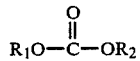

where $R_1$ is

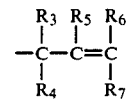

wherein $R_3$-$R_7$ are independently each occurrence hydrogen or a hydrocarbyl radical of up to 20 carbons selected from the group consisting of alkyl, aryl, alkaryl, aralkyl, alkenyl and inertly-substituted derivatives thereof; and $R_2$ is $R_1$ or a hydrocarbyl radical of up to about 20 carbons selected from the group consisting of alkyl, aryl, alkaryl, aralkyl and inertly-substituted derivatives thereof.

By the term "inertly-substituted derivatives" is meant chemical derivatives of the named compounds containing substituents that are unreactive under the reaction conditions and non-interfering with the desired allylation reaction. Suitable inertly-substituted compounds are those compounds that do not contain ionizable carbon-hydrogen bonds. They may be easily identified by routine experimentation. It is already known, for example, that phenol-, carboxy- or amine-containing substituents are unsuitable but that alkoxy, aryloxy, halogen or halogenated alkyl or aryl substituents may be present.

The allyl carbonates for use according to the present invented process are known compounds or else they may be prepared by techniques well-known in the art. Preferred allyl carbonates are those wherein $R_2$ and $C_{1-4}$ alkyl and $R_1$ is allyl or methallyl. Particularly where $R_2$ is $C_{1-4}$ alkyl the byproduct alkanol formed is easily removed from the reaction mixture and in particular is separated from the desired allylated carbon acid.

The carbon acids for use according to the invention are those compounds having at least one acidic carbon-hydrogen bond. By the term "acidic" is meant an ionizable hydrogen giving the compound a pK equal to or less than 25. Representative carbon acids include those compounds listed in Table 9-1 of H. O. House, *Modern Synthetic Reactions*, 494, W. A. Benjaman, Inc., Menlo Park, Calif. (1972) which teaching is incorporated herein by reference. Generally, esters, ketones, alkyl cyanides and nitroalkanes having up to about 20 carbons with at least one α-hydrogen may be allylated. Also suitable are compounds of up to about 20 carbons which contain a terminal acetylene moiety.

The catalysts for use according to the invention include both homogeneous and heterogeneous catalysts. Included as representative are stable phosphine, phosphite, arsine or stibene complexes, and other homogeneous complexes of one of the previously identified metals or complexes of one of the above metals and a polymeric ligand, such as a functionalized styrene divinylbenzene copolymer wherein the functional groups are capable of forming complexes. Preferred ligands are the triorgano phosphines such as trialkyl phosphines of up to about 4 carbons in each alkyl group or triphenyl phosphine.

The metal may be present in the salts form, such as the corresponding metal halide, nitrate or carboxylate or as an organometallic compound. The metal may also be present in the heterogeneous form such as the elemental metal alone or more preferably the metal deposited onto an inert support such as carbon, diatomaceous earth, silica, alumina, zeolites, etc. A preferred support is carbon. Preferably, the amount of such complexing agent added will be from about 0.5 to 4 equivalents per equivalent of metal catalyst based on the stoichiometry of the complex formed.

In one embodiment of the invention, the ligand is added to the reaction mixture containing the metal salt, organometallic compound or heterogeneous metal. Alternatively, the chelated metal catalyst may be first prepared and added directly to the reaction mixture containing the carbonate reactant and carbon acid.

Preferred metals for use in the present invention are nickel and platinum, most preferably present as the elemental metal, especially a supported nickel or platinum metal.

According to the invention, the allyl carbonate, carbon acid and a catalytic amount of the metal catalyst are contacted under an inert atmosphere until the evolution of carbon dioxide ceases. The product may be then recovered by distillation.

The temperature of the reaction may be from about $-20°$ C. to about 150° C. and preferably is from about 20° C. to about 100° C. Reduced or elevated pressures may be employed if desired but no advantage generally results thereby. Preferred is to employ atmospheric pressure and ordinary glass or glass-lined reactor vessels. Reaction times from 0.1 hour to 100 hours may be required depending on the reactants and the reaction conditions employed.

The presence of a solvent is not essential to the reaction but a solvent may be employed if desired to aid in temperature control and in the efficient mixing and contacting of reactants. Ethereal solvents, such as alkyl ethers, polyoxyalkylene ethers and tetrahydrofuran may be used. Other suitable solvents, depending on the nature of the reactants, including aromatic hydrocarbons, ketones, esters, alkyl carbonates, cyanoalkanes, alkanols and chlorinated hydrocarbons.

The amount of catalyst employed is generally from about 0.1 to about 10 percent by weight of metal, preferably from about b 0.1 to about 2 percent.

SPECIFIC EMBODIMENTS

Having described my invention, the following examples are provided as further illustrative and are not to be construed as limiting.

EXAMPLE 1

In a glass flask allyl methyl carbonate (4.0 g, 25 mmole), methyl cyanoacetate (0.99 g, 10 mmole) and tetrakis (triethylphosphite) nickel (0) (0.5 mmole) were combined with stirring and heated to about 23° C. for 15 minutes. In that time evolution of carbon dioxide subsided The reaction was discontinued and the contents of the flask were analyzed by standard techniques of gas-liquid chromatography using an internal standard. The primary reaction product was found to be methyl 2-allyl- -2-cyano-4-pentenoate. 97% yield based on methylcyanoacetate.

EXAMPLES 2-5

The reaction conditions of Example 1 were substantially repeated using allyl methyl carbonate and the carbon acids, catalysts, and reaction conditions further identified in Table I. The primary reaction product and percent yield based on carbon acid are contained in Table I. In Examples 2 and 3, 25 mmoles of allyl methyl carbonate were employed. In Examples 4 and 5, 20 mmoles of allyl methyl carbonate were employed.

TABLE I

| Example | Carbon Acid (mmole) | Catalyst TTPNi[1] (mmole) | Solvent (ml) | Temp (°C.) | Time (hr) | Product (% yield) |
|---|---|---|---|---|---|---|
| 2 | methyl cyanoacetate (10) | 0.3 | — | 70 | 1 | 95[2] |
| 3 | cyano methyl benzene (10) | 0.1 | — | 80 | 1.75 | 90[3] |
| 4 | dimethyl malonate (20) | 0.2 | THF[4] (5.0) | 70 | 2.5 | 94.3[5] |
| 5 | dimethyl malonate (20) | 0.2 | THF[4] (5.0) | 75 | 3.5 | 85[6] |

[1]Tetrakis (triphenyl phosphite)nickel (0)
[2]The product was methyl 2-allyl-2-cyano-4-pentenoate.
[3]The product was a mixture of 50 percent (1-cyano-3-butenyl)benzene and 50 percent (1-cyano-1-allyl-3-butenyl)benzene.
[4]Tetrahydrofuran.
[5]The product was a mixture of 94 percent dimethyl allyl malonate and 6 percent diethyl diallyl malonate.
[6]The product was a mixture of 81 percent dimethyl allyl malonate and 19 percent dimethyl diallyl malonate.

What is claimed is:

1. A process for allylating a carbon acid containing an ionizable carbon-hydrogen bond such that the pK of the carbon acid is equal to or less than 25 which process comprises reacting the carbon acid with an allyl carbonate in the presence of a molybdenum, tungsten, cobalt, nickel, ruthenium, rhodium, osmium, iridium, or platinum catalyst, under conditions such that the carbon acid is allylated.

2. The process of claim 1 wherein the allyl carbonate is of the formula

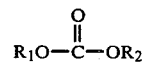

where $R_1$ is

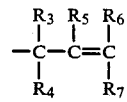

wherein $R_3$–$R_7$ are independently each occurrence hydrogen or a hydrocarbyl radical of up to about 20 carbons selected from the group consisting of alkyl, aryl, alkaryl, aralkyl, alkenyl and inertly-substituted derivatives thereof; and
$R_2$ is $R_1$ or a hydrocarbyl radical of up to about 20 carbons selected from the group consisting of alkyl, aryl, alkaryl, aralkyl and inertly-substituted derivatives thereof.

3. The process of claim 2 wherein $R_2$ is $C_{1-4}$ alkyl and $R_1$ is allyl or methallyl.

4. The process of claim 1 wherein the carbon acid is a compound of up to about 20 carbons selected from the group consisting of a-hydrogen-containing esters, ketones, alkyl cyanides and nitroalkanes and compounds containing terminal acetylene functionality.

5. The process of claim 1 wherein the allylation is conducted at a temperature from about $-20°$ C. to about 150° C.

6. The process of claim 5 wherein the allylation is conducted at a temperature from about 20° C. to about 100° C.

7. The process of claim 1 wherein a solvent is also present.

8. The process of claim 7 wherein the solvent is selected from the group consisting of ethers, aromatic hydrocarbons, ketones, esters, alkyl carbonates, cyanoalkanes, alkanols and chlorinated hydrocarbons.

9. The process of claim 1 wherein the catalyst is a stable complex of the metal and a phosphine, phosphite, arsine, stibene or functionalized polymeric ligand.

10. The process of claim 9 wherein the ligand in a triloweralkyl or triphenylphosphine.

11. The process of claim 9 wherein the metal is nickel or platinum.

12. The process of claim 11 wherein the metal is supported nickel or platinum.

* * * * *